United States Patent
Widera

(10) Patent No.: US 8,064,049 B2
(45) Date of Patent: Nov. 22, 2011

(54) TEST VESSEL AND TEST ARRANGEMENT FOR A MONITORING DEVICE FOR VESSELS

(75) Inventor: Carsten Widera, Aufhausen (DE)

(73) Assignee: Krones AG (DE)

(*) Notice: Subject to any disclaimer, the term of this patent is extended or adjusted under 35 U.S.C. 154(b) by 328 days.

(21) Appl. No.: 12/300,781

(22) PCT Filed: May 9, 2007

(86) PCT No.: PCT/EP2007/004081
§ 371 (c)(1),
(2), (4) Date: Feb. 5, 2009

(87) PCT Pub. No.: WO2007/131673
PCT Pub. Date: Nov. 22, 2007

(65) Prior Publication Data
US 2009/0316145 A1 Dec. 24, 2009

(30) Foreign Application Priority Data
May 13, 2006 (DE) .................. 10 2006 022 492

(51) Int. Cl.
*G01N 21/00* (2006.01)
(52) U.S. Cl. .................. 356/239.4; 356/239.7
(58) Field of Classification Search ........... 356/240.1, 356/243.1, 244, 246, 388–398, 426, 428, 356/239.3–239.6; 382/142
See application file for complete search history.

(56) References Cited

U.S. PATENT DOCUMENTS

| 4,653,907 A * | 3/1987 | Freundlich .................. 356/39 |
| 6,912,303 B2 * | 6/2005 | Heuft .................. 382/142 |
| 2002/0118360 A1 | 8/2002 | Shultz |
| 2005/0172695 A1 | 8/2005 | Furze |

FOREIGN PATENT DOCUMENTS

| DE | 33 24 449 | 1/1985 |
| DE | 41 26 626 | 2/1992 |
| DE | 43 02 656 | 5/1994 |
| DE | 298 03 507 | 2/1998 |
| DE | 196 46 678 | 5/1998 |
| DE | 299 10 452 | 6/1999 |
| DE | 199 46 080 | 5/2000 |
| DE | 100 65 290 | 7/2002 |
| EP | 0 495 647 | 7/1992 |
| GB | 2 094 530 | 3/1982 |
| JP | 4-361142 | 12/1992 |
| JP | 4-367432 | 12/1992 |
| JP | 2003-270166 | 9/2003 |
| WO | WO 98/21566 | 5/1998 |

* cited by examiner

Primary Examiner — Tarifur Chowdhury
Assistant Examiner — Tara S Pajoohi
(74) Attorney, Agent, or Firm — Hayes Soloway P.C.

(57) ABSTRACT

The invention relates to a test vessel (1) for a monitoring device for vessels, comprising a plurality of first marking rings (2) which surround the bottle body (7) at least in some sections at predefined fixed heights, and a plurality of marking lines (4) which run in a longitudinal direction (L) of the test vessel (1). According to the invention, the first marking rings (2) are respectively arranged at constant, predefined distances from one another in the longitudinal direction (L) of the test vessel (1). The marking lines (4) intersect at least some of the first marking rings (2), and the marking lines (4) are respectively arranged at predefined distances from one another in a circumferential direction of the test vessel (1).

14 Claims, 2 Drawing Sheets

TEST VESSEL AND TEST ARRANGEMENT FOR A MONITORING DEVICE FOR VESSELS

The present invention relates to a test vessel and a test arrangement for a monitoring device for vessels. A large number of monitoring devices for vessels are known from the prior art, such as, for example, empty bottle inspection devices, filling level test devices, labelling machines and the like. Such monitoring devices usually have one camera or a plurality of cameras which examine the bottles with regard to various criteria, such as, for example, with regard to the correct arrangement of a label on the bottle, a desired filling level, the bottle contents, the state of the bottle neck and of the bottle rim, and the like. The cameras observe the vessels from different directions. Such devices are described for example in DE 299 10 452 U1, DE 100 65 290 A1, JP 4-367432 A1, JP 4-361142 A1 or JP 2003-270166 A.

In the case of a defect of individual cameras, in each case new cameras have to be used instead of the defective cameras. This requires a very time-intensive and therefore cost-intensive readjustment of the replacement cameras. In particular, care has to be taken to ensure that the respective cameras to be replaced can be changed in the event of a defect without having to make changes to the existing types of production. In order to achieve this, the replacement camera after the change must again have the same mechanical position, the same aperture and also the same zoom and focus as the replaced camera. This replacement of the cameras is a very time-intensive procedure. In addition, the changing of the cameras can usually be carried out only by specialist personnel due to the very high demands placed on the inspection accuracy, and for this reason too it is therefore very complicated.

An object of the present invention is therefore to provide a device which allows an easier readjustment of a camera that is to be changed in a monitoring device for vessels.

The test vessel according to the invention for a monitoring device for vessels comprises a plurality of first marking rings which surround the test vessel at least in some sections at predefined fixed heights. In addition, a plurality of marking lines are provided which run in a longitudinal direction of the test vessel. According to the invention, the first marking rings are respectively arranged at constant, predefined distances from one another in the longitudinal direction of the test vessel, and the marking lines intersect at least some of the first marking rings. Furthermore, the marking lines are respectively arranged at predefined distances from one another in a circumferential direction of the test vessel. Preferably, the first marking rings surround the test vessel essentially completely. If the first marking rings do not completely surround the vessel, the first marking rings are more specifically marking ring segments. Preferably the first marking rings and particularly preferably also the marking lines are arranged on an outer surface of the test vessel.

The test vessel is preferably a test bottle, so that the term test bottle will also be used below in addition to the term test vessel.

Due to the plurality of first marking rings and the marking lines, on the whole a scale is formed in the horizontal and vertical direction of the test bottle. In one preferred embodiment, the marking lines are arranged essentially completely around the test vessel and are respectively arranged at equal distances from one another. In this way, a body is formed which is rotationally symmetrical even with regard to the marking lines and marking rings.

Due to the fact that the marking lines are arranged all the way around the test vessel, the situation can be achieved whereby cameras can be adjusted regardless of their position with respect to the test vessel. Preferably, the depth of the marking rings and marking lines is between 0.5 mm and 4 mm, preferably between 1 mm and 3 mm and particularly preferably in the region of 2 mm. The width of the lines is preferably between 0.5 mm and 2 mm, particularly preferably in the region of 1 mm. Furthermore, it is pointed out that other geometries of the respective lines or rings would also be acceptable. However, care should be taken to ensure that the lines are sufficiently durable and sufficiently resistant to wear.

In a further preferred embodiment, second marking rings are arranged on a bottle neck of the test vessel. These second marking rings preferably essentially completely surround the bottle neck and are arranged at equal constant distances from one another. By virtue of these rings on the bottle neck, it is possible for example to adjust cameras which are used for monitoring the labelling on the bottle neck or for monitoring the filling level. In a further embodiment, marking strips are provided on a bottle mouth of the test vessel, which marking strips are arranged at regular distances from one another. More specifically, these may be radially running lines which particularly preferably intersect in the mouth centre of the bottle neck, thereby forming a "crosshair". This arrangement facilitates a central alignment of a camera which observes the bottle rim. In addition, lines which run in the circumferential direction may also be provided on the bottle rim. This is advantageous for example for those inspection tasks in which ring-shaped evaluation gates in images are required.

In a further preferred embodiment, the test vessel has a light-coloured coating at least in some sections. By coating the test bottle for example with a light RAL colour (e.g. light grey), the aperture of a lens can be adjusted by means of the brightness setting of the camera adjustment means (common tools) in such a way that it corresponds to the desired value or a stored reference value. Advantageously, the test vessel is made from a material selected from a group of materials comprising aluminium, plastics, in particular PVC, or the like. Preferably, the test bottle is made from solid material. The advantage of this embodiment is that the intrinsic weight of the test bottle is greater and therefore the test bottle can be placed in a stable manner on a centring plate.

Preferably, the test vessel has in a base region an engagement element so as to be able to be connected to a centring plate in an essentially fixed position. By virtue of this stationary fixing of the test vessel relative to the centring plate, it is easier to achieve an exact adjustment of the respective cameras.

The present invention also relates to a test arrangement comprising a test vessel of the type described above, wherein the test arrangement comprises a centring plate which fixes the test vessel in a predefined, reproducible position. Preferably, the centring plate has a depression for receiving a base region of the test vessel. In this way, it is possible to achieve a particularly secure hold of the test vessel relative to the centring plate. The reproducible arrangement of the test vessel on the centring plate facilitates an adjustment of new cameras on the basis of reference images recorded earlier.

Advantageously, the centring plate has a second engagement element which is designed in a manner complementary to a first engagement element provided on the test vessel and cooperates therewith. In this way, a rotationally fixed arrangement of the test vessel on the centring plate can also be achieved. Preferably, the engagement element of complementary design is a pin which engages in a blind hole.

In a further preferred embodiment, the centring plate and the test bottle are designed in one piece, for example as an injection-moulded part or as a turned part.

The present invention also relates to a method for calibrating or adjusting monitoring devices for vessels, wherein, in a first step, a reference image of a test vessel of the type described above is recorded, and wherein this test vessel is arranged on a centring plate of the type described above. The recording takes place by means of an image recording device. In a further method step, a test image of the test vessel on the centring plate is recorded by means of a further image recording device.

In a further method step, the test image is compared with the reference image and the monitoring or inspection device is calibrated on the basis of the compared images. More specifically, the method according to the invention is used to calibrate a replacement new camera on the basis of the recorded reference image. Preferably, the same test vessel is used in each case for the recording of the reference image and for the recording of the test image. However, it would also be possible to use a further identical test vessel when recording the test image. The complete method is carried out not within a specific time period but rather initially only the reference image is recorded. The test image is not recorded until it is required, that is to say in particular when a camera has to be replaced.

More specifically, a reference image of a test vessel fixed to a centring plate is recorded at a predefined point in time, defined for example by a triggering of a camera, and is stored in the system. This image can be measured to pixel accuracy using the common tools. When replacing the camera, it is possible to position the camera mechanically with pixel accuracy on the basis of the stored settings, and to adjust the zoom to pixel accuracy according to the settings.

The method according to the invention therefore achieves reproducible zoom settings and reproducible aperture settings in a precise vertical positioning of the camera relative to the test surface. By using the test vessel together with the centring plate, the horizontal position of the camera relative to the test vessel can also be reproduced. In particular, the combination of the test vessel and the centring plate thus allows a change of camera without any changes to the parameters of the set types of product.

Preferably, a plurality of test images are recorded, on the basis of which the calibration is carried out. In this case, the respectively recorded test image can be compared with the reference image in separate comparisons until the replacement camera has been fully adjusted. It is also possible to record the test image essentially continuously and thus also to carry out the comparison with the reference image continuously.

Further advantageous embodiments will emerge from the appended drawings.

Figure 1:
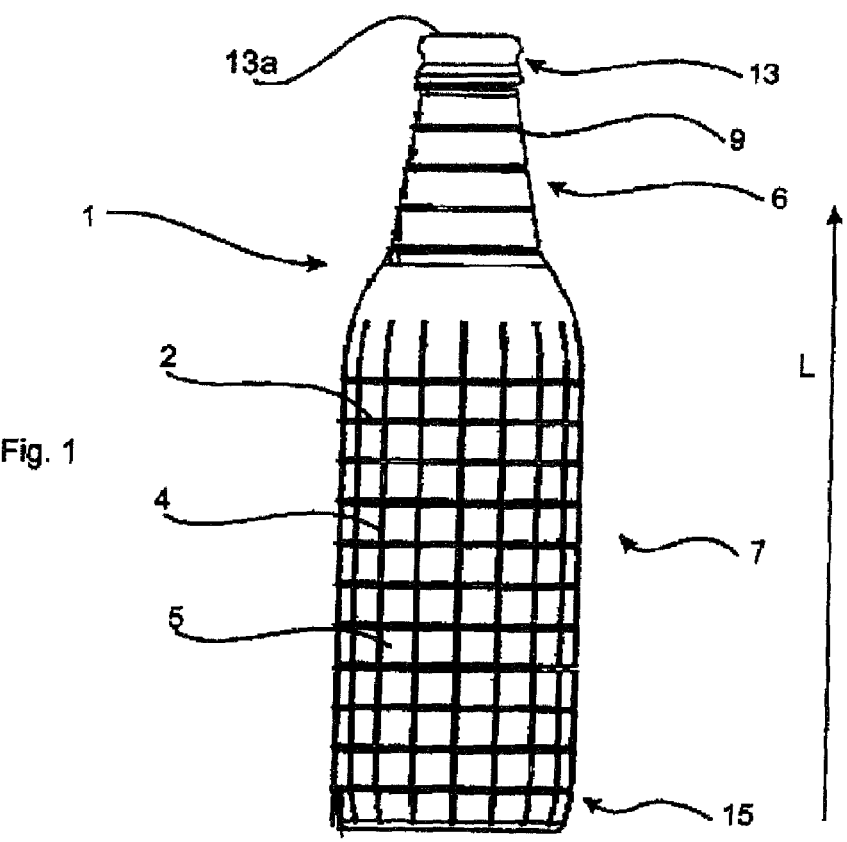
FIG. 1 shows a schematic diagram of a test vessel according to the invention.

FIG. 1 shows a test vessel 1 according to the invention. The test vessel is designed in the form of a test bottle, which comprises a bottle neck 6, a bottle body 7 and a base region 15.

A plurality of marking rings 2 are arranged in the bottle body 7. These marking rings 2 are respectively spaced apart from one another by a distance of 10 mm. Also provided is a plurality of vertical marking lines 4, that is to say lines which extend in the longitudinal direction L of the bottle. The test bottle thus has a horizontal and vertical scale, and therefore individual camera stations such as zoom, focus and brightness can be reproducibly adjusted using this test bottle when a camera or a lens has to be replaced. The use of rings on the one hand and lines on the other hand considerably facilitates the adjustment of cameras, since an orientation in two directions perpendicular to one another is possible.

A plurality of second marking rings 9 are also arranged on the bottle neck 6. In addition, marking lines may also be provided on the bottle mouth 13 and/or on an upper rim 13a (not shown). Radially running lines or also lines running in the circumferential direction would be conceivable on the upper rim 13a.

In one preferred embodiment, different lines are of different colours. In addition, it would also be possible to coat individual grid cells 5, which are formed by the marking rings 2 and the marking lines 4, with different, precisely defined RAL colours over their full surface, such as black, white or certain grey tones. In this way, a brightness comparison for the cameras could be facilitated.

In addition, vertical lines may also be provided on the bottle neck 6, by means of which for example a neck camera can be adjusted. A grid, as mentioned above, may also be provided on the mouth.

Using the test bottle according to the invention, it is possible to adjust in particular camera systems for label inspections, closure inspections, filling level checks, logo detections and the like. In addition, camera systems for side wall inspection, for mouth checking, scuffing (wear) detection or contour detection can also be adjusted.

Figure 2:
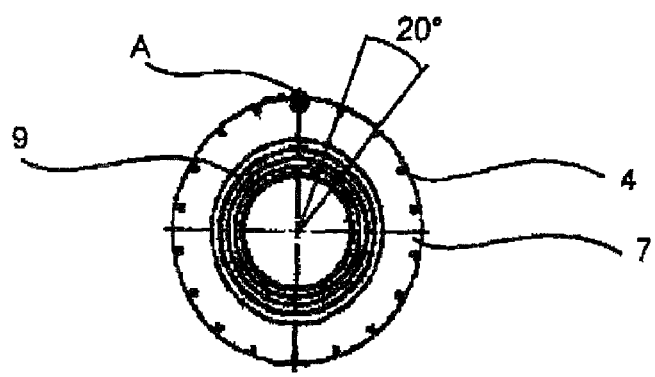
FIG. 2 shows a plan view of the test vessel of FIG. 1.

FIG. 2 shows a plan view of the test bottle of FIG. 1. It can be seen that the individual lines 2 and 4 are in each case cut into the bottle, and that the individual vertical marking lines 4 are in each case spaced apart from one another by equal distances in the circumferential direction. In the present case, the individual lines 4 are spaced apart from one another by 20° in each case, and thus a total of 18 lines are distributed around the entire circumference of the test bottle. The diameter of the bottle here is 62 mm. The second marking rings 9 are concentric in plan view, and the respective changes in radii are essentially constant.

Figure 3:
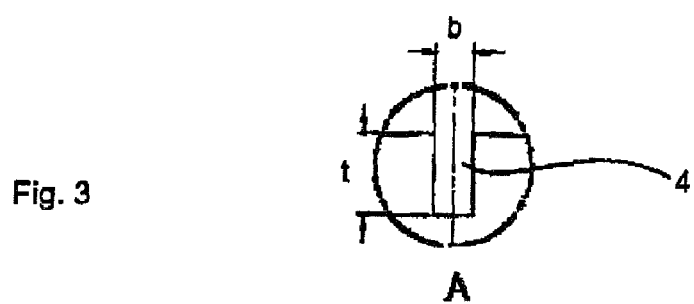
FIG. 3 shows a detail view to illustrate the geometries of the marking lines.

FIG. 3 shows a detail view of a detail from FIG. 2. It can be seen that the individual marking lines and marking rings in this embodiment have a width b of 1 mm and a depth t of 2 mm. However, other dimensions of the individual marking rings and marking lines are also conceivable here. The marking lines and marking rings may also have geometries which differ from one another.

Figure 4:
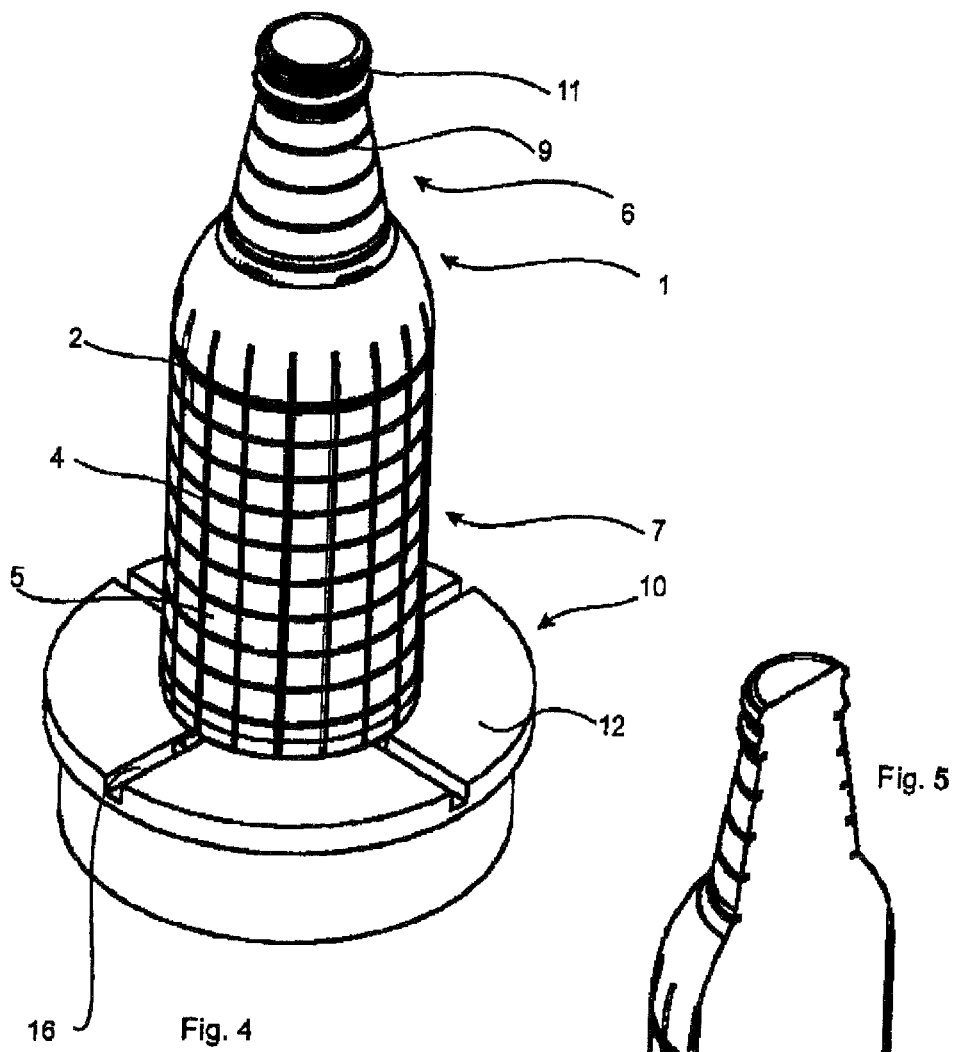
FIG. 4 shows a test arrangement with a test vessel.

FIG. 4 shows a test bottle 1 according to the invention, which is arranged on a centring plate 10. More specifically, the centring plate 10 fixes the test bottle 1 in a predefined position and is in turn itself oriented in a fixed position on a rotatable bottle table, e.g. of a labelling machine, inspection machine or the like. The centring plate has a depression (not shown in FIG. 4) which is designed to match the geometry of the bottle base. The test bottle is inserted into this depression from above. As a result of this insertion, the test bottle 1 is securely fixed with respect to the axis of rotation of the centring plate 10, which coincides here with the axis of symmetry of the vessel. The centring plate 10 here has 4 segments 12, between which grooves 16 are arranged.

Figure 5:
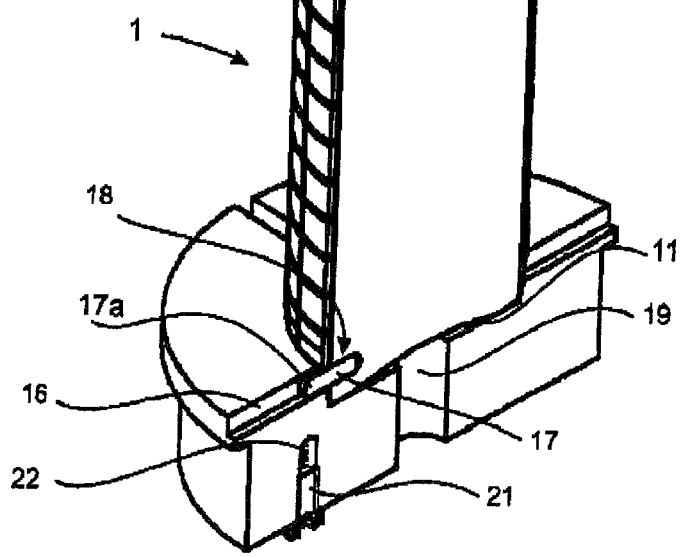
FIG. 5 shows a cut-open view of the arrangement of FIG. 4.

FIG. 5 shows a cut-open view of a test bottle 1 on a centring plate 10. The test bottle 1 has, as shown in FIG. 5, a blind hole 18 in its outer surface and in the vicinity of the base region 15. A dowel pin 17, which lies with its radially protruding part 17a in the abovementioned correspondingly shaped groove 16 in the upper side of the centring plate 10, is inserted into this blind hole 18. Reference 11 denotes a depression of the centring plate 10 for receiving the test bottle 1 or the base region 15 thereof with a precise fit.

In this way, an essentially play-free rotational connection is achieved between the test bottle 1 and the centring plate 10. The dowel pin 17 may additionally have insertion bevels so as to facilitate the arresting of the test bottle.

In the embodiment shown in FIG. 5, the centring plate 10 has a total of four grooves offset from one another by 90° in the circumferential direction. In order to adjust individual cameras, for example in a labelling machine, the centring plate (optionally with the test bottle) is fixed to the plate drive shaft instead of a conventional rotating plate and is rotated by the plate drive motor (not shown) by manual actuation into a defined position of alignment relative to the rotary table. In this position, a circumferential marking on the centring plate coincides with an associated marking on the rotary table, wherein here this may be for example a further blind hole 22 and a further dowel pin 21. The centring plate can then be held in a defined position relative to the rotary table, and then can be moved by the bottle table through the machine to a plurality of cameras. As drives for the centring plate 10, use may be made for example of stepping motors or servo motors. Reference 19 denotes a receiving opening for a pin of the rotary table.

However, further possibilities would also be conceivable for fixing the test bottle 1 relative to the centring plate 10. For instance, the test bottle 1 could also have a thread so as to be screwed into the centring plate 10. In a further preferred embodiment, it would also be possible to design the test bottle 1 and the centring plate 10 in one piece, for example as an injection-moulded part. In this case, too, the position of the test bottle relative to the centring plate would be fixed.

All of the features disclosed in the application documents are claimed as essential to the invention in so far as they are novel individually or in combination with respect to the prior art.

The invention claimed is:

1. A test vessel for a monitoring device for vessels, comprising a plurality of first marking rings which surround the test vessel at least in some sections at predefined fixed heights, and a plurality of marking lines which run in a longitudinal direction (L) of the test vessel, wherein the first marking rings are respectively arranged at constant, predefined distances from one another in the longitudinal direction (L) of the test vessel, the marking lines intersect at least some of the first marking rings, the marking lines are respectively arranged at predefined distances from one another in a circumferential direction of the test vessel, wherein the test vessel has in a base region a first engagement element so as to be able to be connected to a centering plate in an essentially fixed position, wherein the centering plate has a second engagement element which cooperates in a complementary manner with a first engagement element provided on the test vessel, and wherein the first engagement element comprises a recess in a base region of the test vessel and the second engagement element comprises a pin operable to fit into the recess of the first engagement element.

2. The test vessel according to claim 1, wherein the marking lines are arranged essentially completely around the test vessel.

3. The test vessel according to claim 1, wherein second marking rings are arranged on a bottle neck of the test vessel, which second marking rings essentially completely surround the bottle neck and are arranged at equal constant distances from one another.

4. The test vessel according to claim 1, wherein marking strips are provided on a bottle mouth of the test vessel, which marking strips are arranged at regular distances from one another.

5. The test vessel according to claim 1, wherein the test vessel has a light-coloured coating at least in some sections.

6. The test vessel according to claim 1, wherein the test vessel is made from a material selected from the group consisting of aluminum and a plastic.

7. The test vessel according to claim 6, wherein the plastic comprises PVC.

8. A test arrangement comprising a test vessel according to claim 1, further comprising a centering plate which fixes the test vessel in a predefined, reproducible position.

9. The test arrangement according to claim 8, wherein the centering plate has a depression for receiving a base region of the test vessel.

10. The test arrangement according to claim 8, wherein the centering plate and the test vessel are designed in one piece.

11. A method for calibrating monitoring devices for vessels, comprising the steps:

recording, using an image recording device, a reference image of a test vessel which is arranged on a centering plate according to claim 1;

recording, using an image recording device, a test image of the test vessel on the centering plate;

comparing the test image with the reference image and calibrating the monitoring device on the basis of the compared images.

12. The method according to claim 11, wherein a plurality of test images are recorded, on the basis of which the calibration is carried out.

13. The method according to claim 11, wherein the test image is recorded essentially continuously.

14. The test vessel according to claim 1, wherein the test vessel is a bottle.

* * * * *